United States Patent
Wang et al.

(10) Patent No.: US 9,206,152 B2
(45) Date of Patent: Dec. 8, 2015

(54) METHOD FOR EXTRACTING DIHYDROQUERCETIN FROM THE ROOT OF LARCH TREES

(71) Applicant: Liqian Shen, Changchun (CN)

(72) Inventors: Yanjun Wang, Changchun (CN); Yinan Zheng, Changchun (CN); Liguo Shen, Changchun (CN); Yang Shen, Changchun (CN); Liqian Shen, Changchun (CN)

(73) Assignee: Liqian Shen, Jilin (CN)

( * ) Notice: Subject to any disclaimer, the term of this patent is extended or adjusted under 35 U.S.C. 154(b) by 0 days.

(21) Appl. No.: 14/696,332

(22) Filed: Apr. 24, 2015

(65) Prior Publication Data

US 2015/0225362 A1    Aug. 13, 2015

Related U.S. Application Data

(63) Continuation of application No. PCT/CN2013/079583, filed on Jul. 18, 2013.

(30) Foreign Application Priority Data

Oct. 25, 2012  (CN) .......................... 2012 1 0412622

(51) Int. Cl.
C07D 311/40 (2006.01)
C07D 311/32 (2006.01)

(52) U.S. Cl.
CPC ............ C07D 311/40 (2013.01); C07D 311/32 (2013.01)

(58) Field of Classification Search
USPC ........................................................ 549/400
See application file for complete search history.

(56) References Cited

FOREIGN PATENT DOCUMENTS

| CN | 1844095 A | 10/2006 |
|----|-----------|---------|
| CN | 1858046 A | 11/2006 |
| CN | 101333203 A | 12/2008 |
| CN | 101333204 A | 12/2008 |
| CN | 101781277 A | 7/2010 |
| CN | 101851221 A | 10/2010 |
| CN | 101863869 A | 10/2010 |
| CN | 101993429 A | 3/2011 |
| CN | 102924420 A | 2/2013 |

OTHER PUBLICATIONS

Machine translation of CN102924420A (published on Feb. 13, 2013); translated on Jun. 16, 2015.*
Xu, Hong-Yan et al., "Present status and developing trend of isolation and purification on dihydroquercetin from natural products" Food & Machinery, vol. 26, No. 5, Sep. 2010, pp. 173-176.
Wang, Chang et al., "Research Progress of the Sawdust of Larix" Food Research and Development, vol. 33, No. 2, Feb. 2012, pp. 232-236.
International Search Report of corresponding International PCT application No. PCT/CN2013/079583, dated Oct. 31, 2013.
Chinese First Examination Report of corresponding China patent application No. 201210412622.6, dated Jun. 4, 2013.

* cited by examiner

Primary Examiner — Kristin Vajda
(74) Attorney, Agent, or Firm — J.C. Patents

(57) ABSTRACT

The present invention provides a method for extracting dihydroquercetin from roots of larch trees in a specific region by utilizing a resource advantage that the roots (200 mm below the earth surface) of tree species has a relatively high content of dihydroquercetin. The method includes steps of: selecting raw material, processing, extracting, concentrating, hydrolyzing, further extracting and recrystallizing. The present invention has researched and established a process with optimized environmental protection and indexes to fill the gap in domestic industrialized extraction process by utilizing the resource advantage that the roots of tree species has relatively high content of dihydroquercetin.

1 Claim, 1 Drawing Sheet

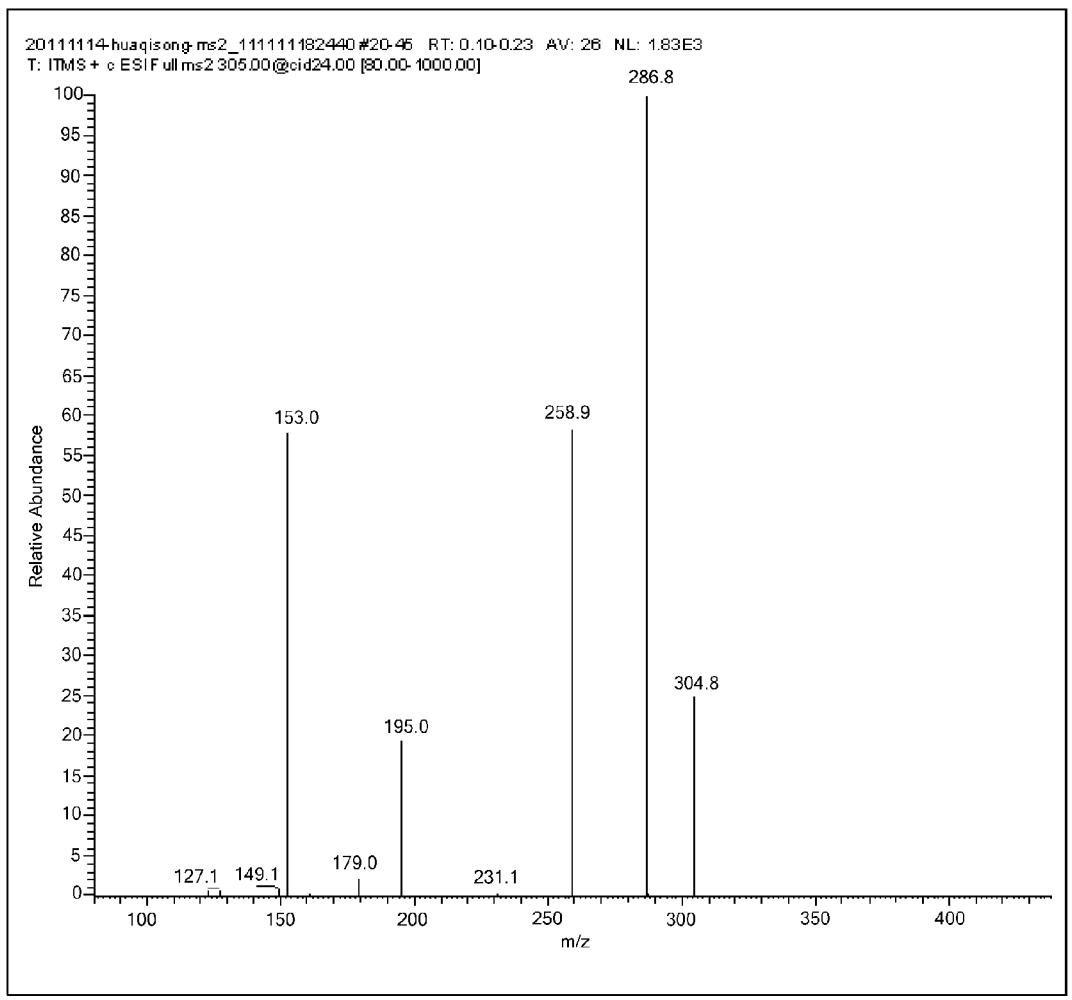

METHOD FOR EXTRACTING DIHYDROQUERCETIN FROM THE ROOT OF LARCH TREES

CROSS-REFERENCE TO RELATED APPLICATIONS

This application is a continuation of International Application No. PCT/CN2013/079583, filed on Jul. 18, 2013, which claims the priority benefit of Chinese Patent Application No. 201210412622.6, filed on Oct. 25, 2012. The contents of the above identified applications are incorporated herein by reference in their entireties.

FIELD OF THE TECHNOLOGY

The present invention relates to a method for extracting dihydroquercetin, and particularly to a method for extracting dihydroquercetin from roots of larch trees.

BACKGROUND

Dihydroquercetin, of which the molecular formula is: $C_{15}H_{12}O_7$, the molecular weight is: 304.26, and the structural formula is: 2-(3,4-dihydroxyphenyl)-2,3-dihydro-3,5,7-trihydroxy-4H-benzopyran-4-one.

The molecular structure of dihydroquercetin is represented as below:

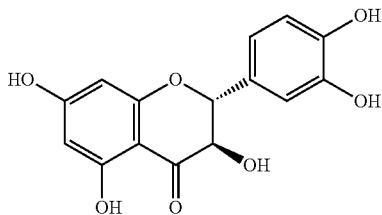 [SMILES: O=C1c2c(O)cc(O)cc2O[C@H](c2ccc(O)c(O)c2)[C@H]1O]

Dihydroquercetin is a type of flavonoid, which is referred to as vitamin P. Dihydroquercetin acts as a powerful antioxidant, which may inhibit activities of active oxygen species (free radicals) in human body, and which has effects of anti-radiation, detoxification and antibody countercurrent and can inhibit peracid oxidation of lipid compounds and lesions in cell membranes. Plant extracts belong to a category of non-synthesized substance.

Application of Dihydroquercetin Covers:

① Comparison in flavonoids: proanthocyanidins, *ginkgo biloba* leaf pigment, seabuckthorn pigment, rutin, morin, hesperidins, quercetin and so on are acknowledged and applied in medical care and treatment, however, dihydroquercetin is powerful in disease prevention besides its therapeutical effect. A medical study has proved that 98% of oxygen inhaled in human body is in normal use, but the rest 2% is converted into free radicals which are extremely active in a chemical reaction, also known as reactive oxygen, they are highly toxic to human life. The free radicals may cause weakened immune ability in human body, premature aging of organs and degradation of the circulation system, while the presence of dihydroquercetin may impede activities of the free radicals and damages resulted therefrom. From a pharmacological perspective, dihydroquercetin is a powerful antioxidant or anti-radiation agent, which has effects of regeneration, detoxification and antibody countercurrent, and which can inhibit peracid oxidation of lipid compounds and lesions in cell membranes.

② Medicament: from a medical and pharmacological perspective, dihydroquercetin has a wide range of applications based on its pharmacological properties, such as medicines for the treatment of cardiovascular diseases and metabolic disorders. At present, Harbin Medical University is developing a new type of medicine using dihydroquecetin.

③ Health care products: for the powerful antioxidant, simple care effects upon ears, teeth and skin are obvious. All corresponding products of Amway and Nu Skin contain dihydroquercetin.

④ Food: dihydroquercetin is used as a bioactive food additive due to its bioactivity and excellent antioxidant activity, so that food and food ingredients are preserved to prolong the shelf-life on one hand, and effects of disease prevention and treatment are increased on the other hand.

⑤ Agriculture: "a plant growth regulator" which takes dihydroquercetin as a major ingredient may reduce impacts from bacteria and fungi upon plant germination, growth and fruiting periods and also enhance cold resistance, drought tolerance and storability thereof. The related "plant growth regulator" has been disclosed by a national invention patent on Feb. 8, 1992 in Russia.

⑥ Industry: the performance of dihydroquercetin is superior to many known antioxidants in use, such as an antivibration agent incorporated in raw materials of jet engines and rocket projectiles, a stabilizer used in raw materials of rockets and hydrocarbons, and an antioxidant for colourant and paint.

Due to resource advantages, Russia has researched in this technical field across the world early and has a mature production process, and the production has been industrialized (with an annual yield of approximately 11 tons in total by three factories). Currently, some teaching and scientific research institutes in China have already conducted research and experiments towards this technique, among which Guangzhou University and Zishan Technology Co., Ltd. in Heilongjiang province have applied for invention patents (both applicants once worked at the same scientific research institute in Heilongjiang Province), but without industrialization records. By comparing contents described in these two patent applications, the common features lie in that, trucks of larch trees growing above the ground for about 40 years old originate from Xing An Ling areas. The distinction lies in that, solvents are different during the extraction, both with water (it is not indicated whether the water is deionized water) and 50% of ethanol respectively. A Russian standard sample is used as standard. Amount of dihydroquercetin in the raw material is not disclosed in the patents, so that the yield cannot be verified. In addition, it is a waste of timber species as all raw materials are selected from stubs growing 500 mm above the ground.

SUMMARY

An objective of the present invention is to provide a method for extracting dihydroquercetin from roots of larch trees in a high yield by utilizing a resource advantage that the roots of tree species (200 mm under the earth surface) have relatively high content of dihydroquercetin, the method is environmental friendly and optimized in various aspects.

The objective of the present invention is achieved by using the method for extracting dihydroquercetin from the roots of larch trees, which includes steps of:

① raw material selection: content of dihydroquercetin in the roots of larch trees selected falls between 2.9%-3.9%;

② raw material cleaning and washing: cutting off the roots of the larch trees selected, removing root hair, washing off dirt and sand with a high-pressure water jet, then air-drying the roots, and storing the same away from light in a relative humidity of 65%;

③ raw material processing: crumbling the raw material stored in step ② into wood pieces with a particle size of 3×3×6 mm and a specific surface area of approximately 16, where fibers are in a torn state;

④ extraction and concentration: using a thermal reflux percolation method, adding the processed wood pieces in step ③ into an extraction tank and adding a mixed solvent consisting of deionized water and acetonitrile at a volume ratio of 1:1, where the wood pieces and the gap in domestic industrialized extraction.

2. The present invention uses roots of larch trees as a raw material, which is considered as recycling of wastes; while the roots belong to wastes of thinning (the life span of this tree species is limited). According to statistics from Ministry of Forestry, utilization rate of a tree (whose age reaches a limit) is 49% currently. The present invention increases the utilization rate of this tree species by 1.2% (i.e., the dried wood pieces after the extraction can be recycled for paper-making and other usage) while driving the scientific research institutes to research and develop useful value of roots of other tree species.

3. The extracts according to the present invention have high purity and high yield.

BRIEF DESCRIPTION OF THE DRAWINGS

FIG. 1 is a mass spectrum of dihydroquercetin.

DETAILED DESCRIPTION

Equipments: a thermal reflux extraction tank (0.5 m$^3$), a vacuum suction single-effect external circulation evaporator (100 L/h), a hydrolysation tank (100 L), an extraction tank (100 L), a ZG-5 vacuum oven, a 2BV5121 water ring vacuum pump and a recrystallization tank (50 L).

Raw material: 35 kilograms of roots obtained from thinning wood of Meixi Forestry Center, Yichun, in an age of 38-42 years old and with dihydroquercetin in an average amount of 3.3%.

Raw material cleaning and washing: cutting off roots of the larch trees selected, removing root hair, washing off dirt and sand with a high-pressure water jet, then air-drying the roots, and storing the same away from light in a relative humidity of 65%;

Raw material processing: crumbling the raw material stored in step ③ into wood pieces with a particle size of 3×3×6 mm and a specific surface area of approximately 16, where the fibers are in a torn state;

Operation Process:

1. Feeding 35 kilograms of raw material into the extraction tank and adding 315 kilograms of mixed solvent consisting of deionized water and acetonitrile at a volume ratio of 1:1, being subject to immersion statically for one hour at a constant temperature when the extraction tank is heated to 60° C.

2. The extracting solution is pumped into the fitted single-effect evaporator under vacuum condition. A first-class condenser equipped for the extraction tank starts working. Switch off the vacuum valve when 50% of the extracting solution is introduced into the evaporator.

3. Adjusting the outlet valve of the extracting solution at a flow rate of 50 L/h, where secondary steam (solution medium) generated from the extraction tank and the evaporator flows through the first-class condenser becoming a liquid phase and backflows to the extraction tank, and a thermal reflux percolation equilibrium is established. The extraction and the concentration process take 3.5 hours, and the operating temperature is 60° C.

4. After the extracting process is completed, a steam heating valve of the extraction tank is switched off meanwhile a steam heating valve of a heater of the evaporator is switched on to proceed with the concentration for the extracting solution, where the operating temperature is 65° C., and the solution medium is recovered. Extracts are collected when the specific gravity of the extracts is 1.05, of which the weight is 9.0 kg.

5. Adding the extracts into the hydrolyzation tank filled with 27 kilograms of purified water, adding hydrochloric acid and stiffing, heating the same when pH value is equal to 6, stirring the mixture for 45 minutes at a constant temperature of 75° C., then cooling the same to the temperature of 30° C., standing for 2 hours.

6. Adding the hydrolysate into the extraction tank filled with 12.6 kilograms of extractant consisting of methyl tert-butyl ether and dioxane at a volume ratio of 1:1, stirring the mixture for 30 minutes at a temperature of 30° C., and standing for 1 hour at a constant temperature of 22° C., then collecting the supernatant for concentration using the single-effect evaporator, recovering the extractant at an atmospheric pressure and at an operating temperature of 45° C. to obtain 1.23 kilograms of yellow powders.

7. Adding the powders into the recrystallization tank filled with 12.3 kilograms of purified water, heating while stirring, further stirring the same for 20 minutes at a constant temperature of 75° C., stopping stirring. Then, a valve for controlling chilled brine kept at an interlayer of the tank is switched on to cool down the liquid within the tank at a temperature of 4° C. 12 hours later, remove the supernatant to obtain 1.69 kilograms of crystals. Collect the crystals in a tray and deliver the same to a vacuum oven for a drying process at a temperature of 65° C. and a vacuum degree of 0.08 MPa. After 12 hours, the sample is taken out and crumbled into powders in a total of 1.11 kg which is identified as dihydroquercetin by MS detection. The detection result is shown in FIG. 1, where the purity level is 99.7% and the yield is 95.8%.

Comparative Example 1

As an extraction solvent, the mixed solvent in step ④ consisting of deionized water and acetonitrile at the volume ratio of 1:1 is replaced with water and 50% ethanol respectively. The remaining process is the same as that in Example 1. The obtained dihydroquercetin has purity levels of 96.7% and 95.9% and yield of 84.1% and 81.2%, respectively.

Comparative Example 2

As an extractant, the mixed solvent in step ⑥ consisting of methyl tert-butyl ether and dioxane at the volume ratio of 3:1 is replaced with methyl tert-butyl ether and dioxane respectively. The remaining process is the same as that in Example 1. The obtained dihydroquercetin has purity levels of 96.1% and 93.8% and yield of 85.3% and 71.2%, respectively.

It can be seen from Example 1 and Comparative Examples 1-2 that, the method described in the present invention can obtain a product with high purity level and high yield.

The invention claimed is:

1. A method for extracting dihydroquercetin from roots of larch trees, comprising steps of:
   ① raw material selection: content of dihydroquercetin in the roots of larch trees selected falls between 2.9%-3.9%;

②  raw material cleaning and washing: cutting off the roots of the larch trees selected, removing root hair, washing off dirt and sand with a high-pressure water jet, then air-drying the roots, and storing a same away from light in a relative humidity of 65%;

③ raw material processing: crumbling the raw material stored in step ② into wood pieces with a particle size of 3×3×6 mm and a specific surface area of approximately 16, wherein fibers are in a torn state;

④ extraction and concentration: using a thermal reflux percolation method to add the wood pieces processed in step ③ into an extracting tank and add a mixed solvent consisting of deionized water and acetonitrile at a volume ratio of 1:1, wherein the wood pieces and the mixed solvent have a weight ratio of 1:10, and extracting temperature is 60° C., using a single-effect external circulation evaporator for concentration, wherein the process should be completed within six hours, collecting extracts when the specific gravity of the extracts is 1.04-1.05;

⑤ hydrolyzation: adding the extracts obtained in step ④ into a hydrolyzation tank filled with water three times the weight thereof, then adding hydrochloric acid and stirring the mixture, heating a same when pH value is equal to 6, stirring the mixture for 45 minutes at a constant temperature of 75° C., then cooling down a same to the temperature of 30° C., and standing for 2 hours;

⑥ further extraction: adding the hydrolysate of step ⑤ into the extraction tank, then adding an extractant consisting of methyl tert-butyl ether and dioxane at a volume ratio of 3:1, wherein the hydrolysate and the extractant have a weight ratio of 1:0.35-0.4, heating while stirring the mixture, further stirring a same for 30 minutes at a constant temperature of 30° C., then following a cooling process, and standing for 1 hour at a temperature of 22° C., then collecting the supernatant;

⑦ concentration: vacuum sucking the supernatant obtained in step ⑥ into the single-effect external circulation evaporator for concentration, removing the extractant under an atmospheric pressure and at a temperature of 45° C., collecting the sample in a form of powder after the extractant is completely removed;

⑧ recrystallization: adding the powders into a crystallization tank, then adding purified water, wherein the powders and the purified water have a weight ratio of 1:10, heating and stirring the mixture, further stirring a same for 20 minutes at a constant temperature of 75° C., following a cooling process after stopping stirring, standing for 12 hours at a constant temperature of 4° C., collecting the crystals in a tray and delivering a same to a vacuum oven; and ⑨ drying: obtaining dihydroquercetin after a 12-hour drying process at a temperature of 65° C. and a vacuum degree of 0.08 MPa.

* * * * *